US005591210A

United States Patent [19]
Kroll et al.

[11] Patent Number: 5,591,210
[45] Date of Patent: Jan. 7, 1997

[54] IMPLANTABLE DEFIBRILLATION SYSTEM AND METHOD FOR PRODUCING ONLY SHORT PULSE WAVEFORMS

[75] Inventors: Mark W. Kroll, Minnetonka; Theodore P. Adams, Edina, both of Minn.

[73] Assignee: Angeion Corporation, Plymouth, Minn.

[21] Appl. No.: 295,230

[22] Filed: Aug. 24, 1994

Related U.S. Application Data

[63] Continuation of Ser. No. 953,485, Sep. 29, 1992, abandoned.

[51] Int. Cl.$^6$ .................................................. A61N 1/39
[52] U.S. Cl. ................................................................. 607/5
[58] Field of Search ..................................... 607/5, 6, 7, 8

[56] References Cited

U.S. PATENT DOCUMENTS 4,708,145  11/1987  Tacker, Jr. et al. ................. 128/419 D
4,953,551   9/1990  Mehra et al. .

FOREIGN PATENT DOCUMENTS 0280526  2/1988  European Pat. Off. .
286108  10/1983  Germany .

OTHER PUBLICATIONS

Cardiac Pacemaker, Inc., St. Paul, MN; Model 1700.
Ventritex, Sunnyvale, CA., "Cadence" tiered therapy defibrillator Model V–100.
Cardiac Pacemakers, Inc., St. Paul, MN; Ventak AICD, cardioverter defibrillator Models 1500,1510,1520.
Medtronic, Inc., "Tachyarrhythmia Management", 1991, Annual Report 1991, pp. 12,13.
Telectronics Pacing Systems, Inc., "Gaurdian ATP", 1990, Product Brochure, p. 1.
Cardiac Pacemakers, Inc., "Advanced AICD Therapy Made Easy", 1991, Product Brochure, pp. 1,2.
Hook et al., Advances in Third–Generation ICD Therapy, Cardio, Nov. 1991 pp. 66–72.

Hammel et al., Implantation of a Cardioverter/Defibrillator in Subpectoral Region combined with a Nonthoracotomy Lead System, Pace, vol. 15, Apr. 1992, pp. 367–368.
Yee et al., Can. J. Cardiol., vol. 6, No. 4, pp. 147–156 (1990).
Rattes et al., American Heart Journal, vol. 111, No. 5, pp. 874–878 (1986).
Kallok et al., Medical Instruments, vol. 20, No. 1, pp. 36–39 (1986).
Kallok et al., Am. Heart J., vol. 109, No. 4, pp. 821–826 (1986).
Jones et al., Circulation, vol. 73, No. 3, pp. 484–491 (1986).
Chang et al., JACC, vol. 8, No. 6, 1393–1405 (1986).
Lang et al., IEEE Engineering in Medicine and Biology Society, vol. 11:1989.
Louis Lapicque, "Experimental Definition of Excitability", Proc. Soc. de Biol., vol. 77, pp. 280–285, 1909.
Geddes, L. A. and Tacker, W. A., Med. & Biol. Engng., vol. 9, pp. 185–199.

(List continued on next page.)

*Primary Examiner*—George Manuel
*Assistant Examiner*—Scott M. Getzow
*Attorney, Agent, or Firm*—Patterson & Keough, P.A.

[57] ABSTRACT

The present invention provides a biophysical-electronic system and method embodied in a defibrillation system with a range of pulse durations under 6 milliseconds, which is precisely the optimal range. The present invention provides an implantable defibrillator that delivers such waveforms. The present invention specifies optimal pulse duration for a given capacitor size, a determination that takes into account both the time constant of the system and the characteristic time (chronaxie) of the cardiac tissue. In addition to enhancing defibrillation effectiveness, the present invention provides size reduction in the implantable system, or the increased battery (and hence system) life, or some of both. The lower-energy shocks also reduce tissue damage from defibrillation procedures.

14 Claims, 3 Drawing Sheets

OTHER PUBLICATIONS

Geddes, L. A. et al., Med. & Biol. Engng. & Computing, vol. 23, No. 2, London, Great Britian, pp. 120–130.

Lang, Douglas J., et al. Strength–Duration Relationship For Biphasic Defibrillation in Dogs, IEEE, 1989.

G. Weiss, "Sur la possibilite' de rendre comparable entre eux les appareils survant a l'excitation electrique," *Arch. Ital. de Biol.*, vol. 35, pp. 413–446, 1901.

H. Fredericq, "Chronaxie: Testing excitability by means of a time factor," *Physiol. Rev.*, vol. 8, pp. 501–545, 1928.

L. Lapicque, "Definition experimentalle de l'excitabilite'," *Proc. Soc. de Biol.*, vol. 77, pp. 280–285, 1909.

J. D. Bourland, W. A. Tacker, and L. A. Geddes, "Strength duration curves for trapezoidal waveforms of various tilts for transchest defibrillation in animals," *Med. Instr.*, vol. 12 #1, pp. 38–41, 1978.

J. D. Bourland, W. A. Tacker, L. A. Geddes, et al, "Comparative efficacy of damped sine wave and square wave current for transchest ventricular defibrillation in animals," *Medical Instrum.*, vol. 12 #1, pp. 38–41, 1978.

L. A. Geddes, M. J. Niebauer, C. F. Babbs, et al, "Fundamental criteria underlying the efficacy and safety of defibrillating current waveforms," *Med Biol Eng Comp*, vol. 23, pp. 122–130, 1985.

J. H. Gold, J. C. Schuder, H. Stoeckle, et al, "Transthoracic ventricular defibrillation in the 100 Kg calf with unidirectional rectangular pulses," *Circulation*, vol. 56 #5, pp. 745–750, Nov. 1977.

J. L. Wessale, J. D. Bourland, W. A. Tacker, et al, "Bipolar catheter defibrillation in dogs using trapezoidal waveforms of various tilts," *J Electrocardiology*, vol. 13(4), pp. 359–366, 1980.

J. L. Jones and R. E. Jones, "Determination of safety factor for defibrillator waveforms in cultured heart cells," *Am J Physiol*, vol. 242, pp. H662–H670, 1982.

M. J. Niebauer, C. F. Babbs, L. A. Geddes, et al, "Efficacy and safety of defibrillation with rectangular waves of 2 to 20–milliseconds duration," *Crit. Care Medicine*, vol. 11 #2, pp. 95–98, Feb. 1983.

S. A. Feeser, A. S. L. Tang, K. M. Kavanagh, et al, "Strength–duration and probability of success curves for defibrillation with biphasic waveforms," *Circulation*, vol. 82, pp. 2128–2141, Dec. 1990.

G. Koning, H. Schneider, A. J. Hoelen, et al, "Amplitude–duration relation for direct ventricular defibrillation with rectangular current pulses," *Med Biol Eng*, vol. 13, pp. 388–395, May 1975.

J. L. Jones, R. E. Jones, and G. Balasky, "Improved cardiac cell excitation with symmetrical biphasic defibrillator waveforms," *Am J Pysiol*, vol. 253, pp. H1418–H1424, 1987.

A. S. Tang, S. Yabe, M. Wharton, et al, "Ventricular defibrillation using biphasic waveforms: the importance of phasic duration," *J Am Coll Cardiol*, vol. 13, pp. 207–214, Jan. 1989.

The PCD Tachyarrhythmia Control Device, Model 7217B Device for the control of Ventricular Arrhythmias Through Pacing, Cardioversion and Defibrillation, Medtronic, Inc. Mar. 1990.

IMPLANTABLE DEFIBRILLATION SYSTEM AND METHOD FOR PRODUCING ONLY SHORT PULSE WAVEFORMS

CROSS REFERENCES TO CO-PENDING PATENT APPLICATIONS

This application is a continuation of Ser. No. 07/953,485 filed Sep. 29, 1992, now abandoned.

This patent application is related to U.S. patent application Ser. No. 07/835,836, filed Feb. 18, 1992, entitled "Optimal Pulse Defibrillation Method for Implantable Systems", now U.S. Pat. No. 5,431,686; U.S. patent application Ser. No. 07/808,722, filed Dec. 17, 1991, entitled "Small-Capacitance Defibrillation Process", now U.S. Pat. No. 5,342,399; and U.S. patent application Ser. No. 07/854,862, filed Mar. 19, 1992, entitled "Improved Electrode System for Implantable Defibrillator, now U.S. Pat. No. 5,376,103.

BACKGROUND OF THE INVENTION

1. Field of the Invention

The present invention relates generally to defibrillation processes and waveforms, and more particularly, to truncated and optimally short capacitance-discharge pulses that are attuned to the natural time constants of the system and of the heart, and are delivered by an implantable cardioverter-defibrillator (ICD) or implantable defibrillator.

2. Description of the Prior Art

Present-day defibrillators and ICDs deliver defibrillation shocks of high energy with pulse durations ranging from 6 to 12 milliseconds. These pulses may be monophasic (consisting of a single pulse of a single polarity), as in FIGS. 1A and 1B. Also, the pulses may be biphasic (consisting of a pair of contiguous opposite-polarity pulses), as in FIG. 2, in which case the duration of the first pulse is from 6 to 12 milliseconds. A sampling of product available currently from five vendors is given in Table 1, with an indication of the properties of the pulses they deliver:

TABLE 1

| Vendor | Waveform | Duration phase 1 | Duration phase 2 |
|---|---|---|---|
| Ventritex | Monophasic | 6 ms | |
| Ventritex | Biphasic | 6 | 6 ms |
| Telectronics | Monophasic | * | |
| Medtronic | Monophasic | Programmable** | |
| Intermedics | Biphasic | 6.5 | 3.5 |
| CPI | Monophasic | 65% tilt*** | |

*The Telectronics output is 4, 6, 8, or 12 ms depending on the energy setting for their model 4202 and 4203. The model 4210 has widths of 4, 6, and 11.5.
**Pulse duration can be selected by the implanting physician, but the recommendation is to adjust duration so that a "tilt" of 0.65 obtains, where tilt = $(V_{initial} - V_{final})/V_{initial}$. For the typical value of 50 ohms for the interelectrode resistance, a tilt of 0.65 (or 65%, as it is often expressed) corresponds to 6 milliseconds.
***The pulse duration that accompanies a given tilt specification (see FIG. 1B), is a function of the interelectrode resistance and the value of the capacitor employed for the discharge. For the typical value of 50 ohms for the interelectrode resistance, and the value of 140 microfarads employed by CPI, the resulting pulse duration is 7 milliseconds.

While it is technically possible to program some present-day defibrillation systems for delivery of pulses with a duration shorter than 6 milliseconds, the manufacturers universally recommend using pulses above that range. The novelty, nonobviousness, and benefits of designing systems that deliver only shocks with durations in the range below 6 milliseconds are described in the Summary of the Invention below.

Determining Cardiac Chronaxie. A study and analysis of prior art data on tissue stimulation and defibrillation indicates that the conventionally recommended range of pulse durations exceeding 6 milliseconds is wide of the mark, as is shown here and also in the Summary of the Invention. The subject has a long history. In the late 19th century, Weiss found a linear relationship between the amount of charge needed for the stimulation of tissue by means of an electrical pulse, and the duration of the pulse. [G. Weiss, "Sur la Possibilité de Rendre Comparable entre Eux les Appareils Suivant a l'Excitation Electrique", *Arch. Ital. de Biol.*, Vol. 35, p. 413, 1901.] His pulse generator, the ballistic-rheotome, comprised a dc source and a rifle shot of known velocity that first cut a shunting wire and then a series wire with a known distance between the wires, thus initiating and then ending a rectangular pulse of current. [H. Fredericq, "Chronazie: Testing Excitability by Means of a Time Factor", *Physiol. Rev.*, Vol. 8, p. 501, 1928.] He reported that the charge Q required for stimulation by a pulse of duration d was given by:

$$Q = k_1 d + k_2 \qquad \text{Eq. 1}$$

Subsequently, Lapicque divided the Weiss equation by d, thus obtaining the average current required for stimulation [L. Lapicque, "Definition Experimentelle de l'excitabilite," *Proc. Soc. de Biol.*, Vol. 77, p. 280, 1909.], which can be written:

$$I_{ave} = K_1 + (K_2/d) \qquad \text{Eq. 2}$$

Lapicque also defined two useful terms. The current $I_r$ that would suffice for tissue stimulation by a pulse of infinite duration, he termed the rheobase. Shortening the pulse required progressively more current, and the pulse duration that required a doubling of current for excitation, or $2I_r$, he termed the chronaxie, $d_c$. Placing $2I_r$ and $d_c$ into Eq. 2 in place of $I_{ave}$ and d yields $$d_c = K_2/K_1 \qquad \text{Eq. 3}$$

Factoring $I_r$ out of Eq. 2, and then making use of Eq. 3 yields $$I_{ave} = I_r(1 + d_c/d). \qquad \text{Eq. 4}$$

Lapicque's model described cell stimulation, rather than defibrillation. But in 1978, Bourland, et al., demonstrated that defibrillation thresholds in dogs and ponies followed the Weiss-Lapicque model, provided average current is used in the exercise. [J. D. Bourland, W. Tacker, and L. A. Geddes, "Strength-Duration Curves for Trapezoidal Waveforms of Various Tilts for Transchest Defibrillation in Animals," *Med. Instr.*, Vol. 12, p. 38, 1978.] In another paper, the same workers (with others) showed that average current, $I_{ave}$, is a useful measure of defibrillation effectiveness for time-truncated pulses of a given duration (see FIG. 1A) through a substantial range of durations, from 2 to 20 milliseconds. [J. D. Bourland, W. Tacker, and L. A. Geddes, et al., "Comparative Efficacy of Damped Sine Waves and Square Wave Current for Transchest Defibrillation in Animals," *Med Instr.*, Vol. 12, p. 42, 1978.] In other words, so long as the "tail" of a capacitor-discharge pulse is eliminated, its effectiveness is only a little dependent upon waveform details.

U.S. Pat. No. 4,708,145 to Tacker, Jr., et al. illustrates a representative patent for controlling cardiac ventricular fibrillation.

SUMMARY OF THE INVENTION

The defibrillation chronaxie for the heart is consistently found to fall in the range from 2 to 4.1 milliseconds, as can be seen in Table 2. Citations for the seven papers employed are given below the table. Some of these papers give a curve of average current needed for defibrillation versus pulse duration (a so-called "strength-duration" curve), from which chronaxie can be directly read. In the papers without such a curve, it was necessary to calculate from other given data. In the Geddes, et al. paper (6), strength-duration curves were given for pulses of various tilt, but the results did not vary widely, so they were averaged. For the entire table, the average chronaxie value is 2.7±0.9 milliseconds.

TABLE 2

Summary of Chronaxie Values Read and Inferred from the Literature

| Biblo. | Animal ( ) (electrodes) | Chronaxie | How Determined |
|---|---|---|---|
| 1. | Calf (chest) | 2.7 ms | Calculation |
| 2. | Pony (chest) | 3.6 | Calculation |
| 3. | Dog (endocardial catheter) | 1.8 | From curve |
| 4. | Cultured chick cells in diastole | 1.8 | From curve |
| 5. | Dog (isolated heart in fluid bath) | 4.1 | Calculation |
| 6. | Dog (isolated heart in fluid bath) | 2.8 | From avgd |
| 7. | Dog (epicardial patches) | 2.0 | Calculation |

1. J. H. Gold, et al., Circulation, Vol. 56, p. 745, 1977.
2. J. D. Bourland, et al., Med. Instr., Vol. 12, p. 38, 1978.
3. J. L. Wessale, et al., J. Electrocardiology. Vol. 13, p. 359, 1980.
4. J. L. Jones and R. E. Jones, Am. J. Physiol., Vol. 242, P. H662, 1982.
5. M. J. Niebauer, et al., Crit. Care Medicine, Vol. 11, p. 95, 1983.
6. L. A. Geddes, et al., Med. Biol. Eng. Comp., Vol 23, p. 122, 1985.
7. S. A. Feeser, et al., Circulation, Vol. 82, p. 2128, 1990.

Additional excellent studies of the chronaxie for defibrillation and for diastolic far-field stimulation have also been published. [G. Kining, H. Schneider, A. J. Hoelen, et al., "Amplitude-Duration Relation for Direct Ventricular Defibrillation with Rectangular Current Pulses," *Med. Biol. Eng.*, Vol. 13, p 388, 1975; J. L. Jones, R. E. Jones, G. Balasky, "Improved Cardiac Cell Excitation with Symmetrical Biphasic Defibrillator Waveforms," *Am. J. Physiol.*, Vol 253, p. H1424, 1987; A. S. Tang, S. Yabe, M. Wharton, et al., "Ventricular Defibrillation Using Biphasic Waveforms: the Importance of Phasic Duration," *J. Am. Coll. Cardiol.*, Vol. 13, p. 207, 1989.]

Defining Effective Current. The present invention has developed an analytic method for waveform optimization. It builds upon the models of Lapicque and Weiss, and the findings of Bourland et al. Solving Eq. 4 for the rheobase current yields $$I_r = [I_{ave}/(1+d_c/d)].$$  Eq. 5

Thus, one has here a right-hand-side expression in the two pulse-characterizing quantities $I_{ave}$ and $d$, and in one heart-characterizing quantity, $d_c$, the chronaxie time. Note that for an infinite pulse duration, this current simply equals the average current $I_{ave}$, but for a pulse of finite duration, it will be less than $I_{ave}$. This current, therefore, measures the effectiveness of a particular waveform in defibrillating a particular heart. For this reason the inventors have renamed it the effective current or $I_e$, so that the defining equation is $$I_e = [I_{ave}/(1+d_c/d)].$$  Eq. 6

Note further that $I_e$ would be the same as $I_{ave}$ if one had a zero value of chronaxie time, $d_c$. In this sense, Eq. 6 constitutes a correction from actual average current necessitated by the chronaxie phenomenon. The effective current $I_e$ can be expressed in several ways:

$$I_e = [I_{ave} d/(d_c+d)] = [(\text{delivered charge})/(d_c+d)] = CV_i(\text{tilt ratio})/(d_c+d).$$  Eq. 7

The task that must be addressed next is determining the optimal pulse duration for the conventional time-truncated capacitor-discharge monophasic waveform, specified either by citing duration itself (FIG. 1A), or by citing tilt (FIG. 1B). The resulting specification can equally be applied to the first phase of a biphasic waveform (FIG. 2), or of a multiphasic waveform. A capacitor C will be charged to a voltage $V_i$ and discharged into a load resistance R and then truncated after the duration d. Let us assume that average current and duration of the single phase being considered by themselves provide a sufficient characterization.

Because the waveform is a declining exponential function, and given that $RC=\tau$, the system time constant, tilt as a decimal fraction can be written as follows:

$$\text{tilt} = 1 - \exp(-d/\tau).$$  Eq. 8

Combining Eqs. 7 and 8 yields $$I_e = CV_i[1-\exp(-d/\tau\psi)]/(d_c+d).$$  Eq. 9

It is clear the $I_e$ vanishes at both extremes of d, so the intermediate extremum must be a maximum, defining explicitly the optimum waveform that can be achieved by varying pulse duration with a particular average current. To determine this optimum pulse duration, set $$(dI_e/dd)=0=\{CV_i(d_c+d)[1/\tau\exp(-t/\tau)]-[1-\exp(-t/\tau)]\}/(d_c+d)^2.$$  Eq. 10

Hence, $$0 = \exp(-t/\tau)[(d_c+d)/\tau] - 1 + \exp(-t/\tau)$$  Eq. 11
$$= -1 + \{[(d_c+d)/\tau] + 1\}\exp(-t/\tau).$$

Using the system time constant=RC for normalization yields $$z = d/\tau,$$  Eq. 12 and $$a = d_c/\tau.$$  Eq. 13

Using these definitions, $$(z+a+1)[\exp(-z)]-1=0.$$  Eq. 14

Next multiply through by $-e^{-z}$ to obtain the simplified equation whose root is sought:

$$[\exp(-z)]-z-a-1=0=f(z).$$  Eq. 15

Because the equation is transcendental, it cannot be solved in closed form, so define the function on the left-hand side as f(z) and the first approximation for its root as $z_o$. The Newton-Raphson method gives an approximate value for the root as $$z' = z_o - f(z_o)/f'(z_o).$$  Eq. 16

Experience shows that waveforms with a tilt of about 65% are effective, and this corresponds to $d \approx \tau$, or $z_o=1$. Hence an appropriate approximate root is $$z' = [z_o - f(z_o)/f'(z_o)] = 1-(e-1-1-a)/(e-1) = 1+a/e-1.$$  Eq. 17

Denormalization yields $$d \approx \tau[(1=dc)/\tau]e-1 \qquad \text{Eq. 18}$$

for the approximate optimum value of pulse duration d as a function of chronaxie $d_c$ and system time constant. Using Eq. 18, we next calculate the optimal pulse duration for various values of the capacitor C, assuming a chronaxie of 2.7 milliseconds and a load resistance of 50 ohms. The same information is plotted in FIG. 3.

TABLE 3

| Capacitance | Optimal pulse duration |
| --- | --- |
| 10 microfarads | 1.86 milliseconds |
| 20 | 2.15 |
| 30 | 2.44 |
| 40 | 2.74 |
| 50 | 3.03 |
| 60 | 3.32 |
| 70 | 3.61 |
| 80 | 3.90 |
| 90 | 4.19 |
| 100 | 4.48 |
| 110 | 4.77 |
| 120 | 5.06 |
| 130 | 5.35 |
| 140 | 5.65 |

As noted above, it is technically possible to program some present-day defibrillation systems for delivery of pulses with a duration shorter than 6 milliseconds, but the manufacturers universally recommend using pulses above that range. Or, in the case of Telectronics, force the wide pulse for the most powerful, and hence, important pulse.

The implantable defibrillator or ICD of the present invention is programmable only for pulse durations in the range below 6 milli-seconds. This brings substantial benefits. First, the shorter defibrillation shocks are more effective than the longer shocks of the prior art, as has been shown by our mathematical analysis of the biophysical-electronic system involved. Second, because shorter pulses carry less energy, a system of a given life can be engineered with smaller physical size, through reductions in both battery and capacitor sizes. This in turn affords more freedom and flexibility in the choice of implantation site, with the possibility of pectoral implantation specifically included, and carrying with it the advantage of shorter leads and the possibility of using the housing of the primary module as an electrode.

The third advantage of the reduced energy requirement in the present invention is the option of achieving longer battery life and hence longer system life if system size is kept the same or only partly reduced. A fourth advantage, if one chooses to design for it, is the delivery of pulses of lesser tilt, or more nearly rectangular pulses; the rectangular waveform is known to constitute the ideal shape for defibrillation. Finally, the reduction of energy delivered by the systems and waveforms of the present invention will diminish damage to cardiac tissue resulting from defibrillation shocks administered either appropriately or inappropriately.

The failure of other workers to capitalize on these benefits of shorter defibrillation pulses is puzzling. In spite of the strong hints contained in Table 2, which summarizes finding with animals, transferral of the benefits to humans has not been addressed before, and implantable systems such as that of the present invention have not been previously engineered. These two facts have probably been mutually reinforcing. Another impediment has been the widely held misperception that "enough" energy is an absolute requisite for defibrillation. In the face of this failure of understanding, the benefits from shorter, lower-energy defibrillation shocks have been completely overlooked.

The present invention provides an implantable ICD or else an implantable defibrillator. Either is capable of providing a shock of various waveforms. In the first case, the waveform constitutes a monophasic pulse with a duration of 6 milliseconds or less. Such a pulse can be specified by citing pulse duration directly (see FIG. 1A), or by citing tilt (see FIG. 1B). In the second case, the waveform constitutes a biphasic pulse (see FIG. 2) with the first phase having a duration of 6 milliseconds or less. And in the third case, the waveform is multiphasic, intended here to mean "having three or more phases." In this case, once more, the first phase has a duration of 6 milliseconds or less.

One significant aspect and feature of the present invention is an implantable defibrillator system that delivers a monophasic shock with a duration of 6 milliseconds or less.

Another significant aspect and feature of the present invention is an implantable defibrillator system that delivers a biphasic shock in which the first phase has a duration of 6 milliseconds or less.

Still another significant aspect and feature of the present invention is an implantable defibrillator system that delivers a multiphasic shock in which the first phase has a duration of 6 milliseconds or less.

Yet another significant aspect and feature of the present invention is an implantable ICD system that delivers a monophasic defibrillation shock with a duration of 6 milliseconds or less.

Still another significant aspect and feature of the present invention is an implantable ICD system that delivers a biphasic defibrillation shock in which the first phase has a duration of 6 milliseconds or less.

Another significant aspect and feature of the present invention is an implantable ICD system that delivers a multiphasic defibrillation shock in which the first phase has a duration of 6 milliseconds or less.

Still another significant aspect and feature of the present invention is improved effectiveness of defibrillation administered by an implantable system.

Yet another significant aspect and feature of the present invention is longer battery and system life.

Still another significant aspect and feature of the present invention is an implantable system of less physical size.

A further significant aspect and feature of the present invention is reduced tissue damage associated with defibrillation.

Having thus described embodiments and features of the present invention, it is a principal object of the invention to achieve improved effectiveness in an implanted ICD system or implanted defibrillation system.

Another object of the invention is to extend system life.

A further object of the invention is to reduce the physical size of an implanted system.

A still further object of the invention is to provide for the delivery of monophasic, or biphasic, or multiphasic waveforms.

A still further object of the invention is to determine and demonstrate the optimal combination of capacitor size and pulse duration for defibrillation.

A still further object of the invention is to assemble and apply important data on the characteristic time associated with cardiac tissue for purposes of optimizing a defibrillation procedure.

A still further object of the invention is to diminish tissue damage resulting from a defibrillation procedure.

BRIEF DESCRIPTION OF THE DRAWINGS

Other objects of the present invention and many of its attendant advantages will be readily appreciated as the invention becomes better understood by reference to the following descriptions, when considered in connection with the accompanying drawings, and wherein.

DETAILED DESCRIPTION OF THE DRAWINGS

Figure 1A:
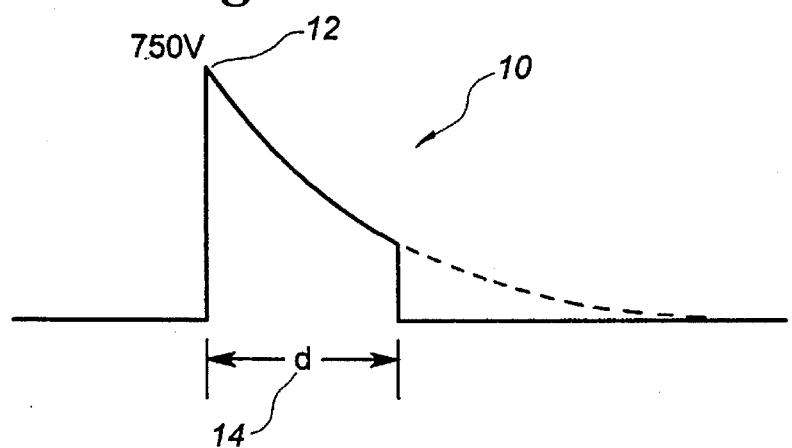
FIG. 1A illustrates a monophasic pulse for defibrillation specified by means of pulse duration d.

FIG. 1A illustrates a waveform 10, constituting a monophasic pulse for defibrillation, which for a given capacitor is fully specified by means of citing initial voltage 12 and duration 14.

Figure 1B:
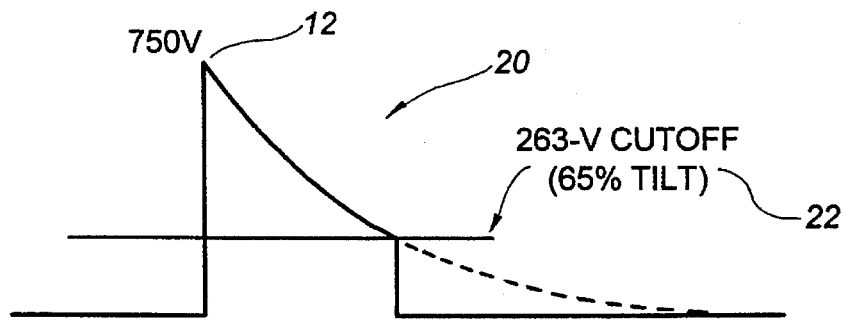
FIG. 1B illustrates a monophasic pulse for defibrillation specified by means of tilt.

FIG. 1B illustrates a waveform 20, constituting a monophasic pulse for defibrillation, which for a given capacitor is fully specified by means of citing initial voltage 12 and tilt 22.

Figure 2:
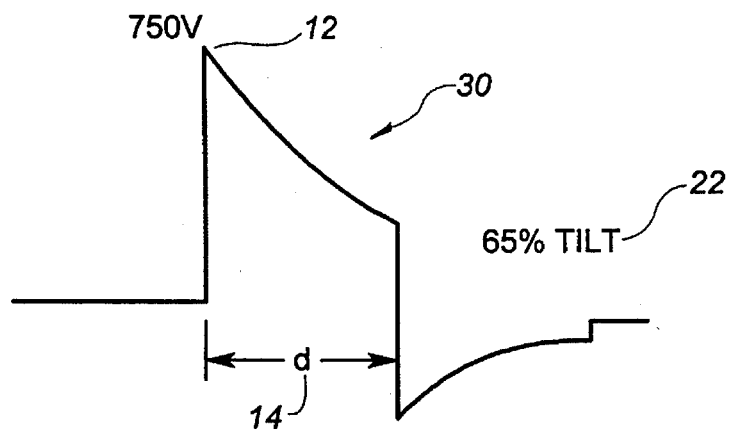
FIG. 2 illustrates a biphasic waveform for defibrillation.

FIG. 2 illustrates a waveform 30, constituting a biphasic pulse for defibrillation, in which for a given capacitor the first phase is fully specified by means of citing initial voltage 12 and duration 14, or else by citing initial voltage 12 and tilt 22.

Figure 3:
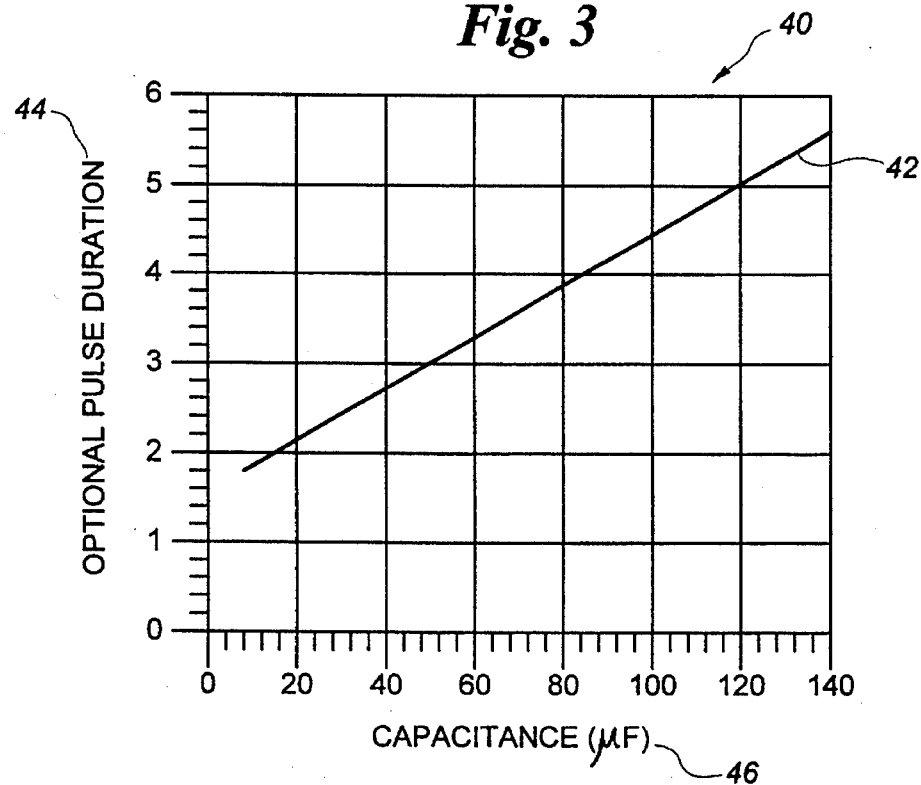
FIG. 3 illustrates graphically the linear functional relationship between optimal pulse duration and capacitor size.

FIG. 3 constitutes a functional plot 40 of the linear relationship 42 between optimal pulse duration 44 and capacitor value 46.

Figure 4:
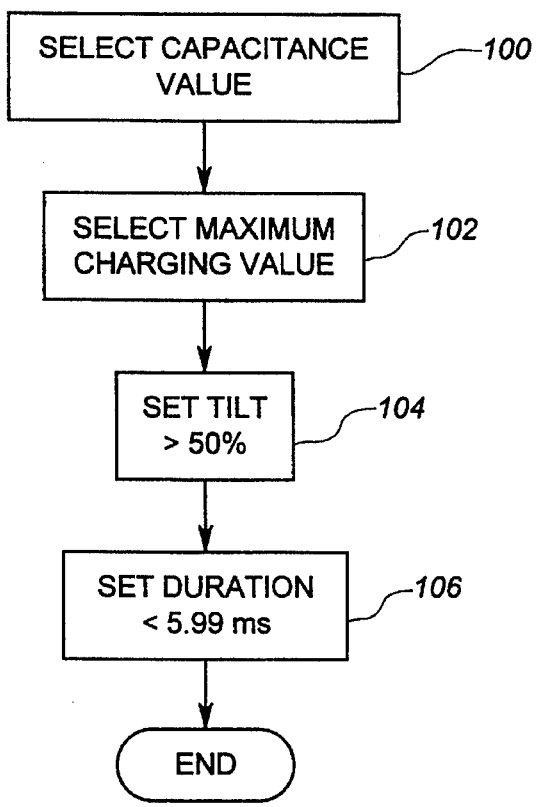
FIG. 4 illustrates a flowchart showing a preferred process of the present invention.

FIG. 4 illustrates a flowchart showing a preferred process of implementing the present invention in an implantable defibrillator system. At step 100, the capacitance value of the pulse-generating capacitor means for the implantable defibrillator system is selected. At step 102, the maximum voltage value to which the pulse-generating capacitor will be charged is selected such that the delivered energy of the countershock is less than 25 joules. At step 104, the tilt of the electrical countershock is selected to be greater than 50%. Finally, at step 106, the duration of the electrical countershock is set at less than 5.99 milliseconds.

Figure 5:
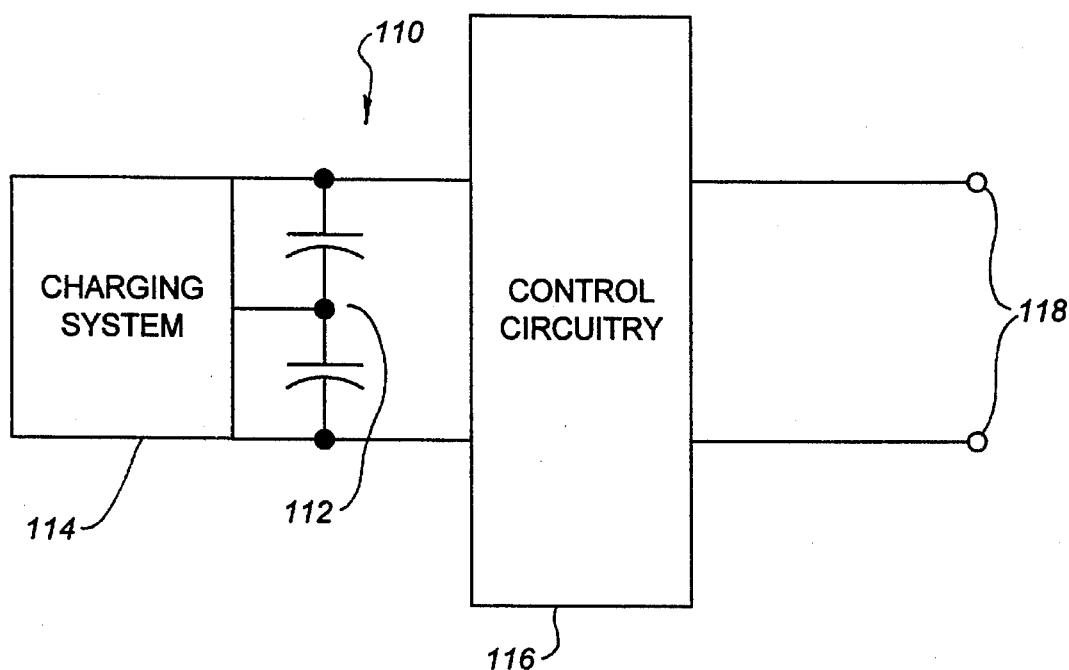
FIG. 5 illustrates a block diagram of a preferred embodiment of an implantable defibrillator system incorporating the present invention.

FIG. 5 illustrates a block diagram of an implantable defibrillator system 110 incorporating the present invention. Implantable defibrillator system 110 is a self-contained human implantable device including a pulse-generating capacitor unit 112 for storing an electrical charge, a charging system 114 for internally charging pulse-generating capacitor unit 112, and control circuitry 116 for selectively discharging the electrical charge in pulse generating capacitor unit 112 for a specified duration as an electrical countershock to be delivered through electrodes 118 implanted in a human patient. Pulse generating capacitor unit 112 and charging system 114 are selected such that the effective capacitance value and maximum charging voltage combine to produce a countershock having a maximum delivered energy of less than 25 Joules. Control circuitry 116 preferrably includes a microprocessor which controls discharge of the electrical charge in pulse generating capacitor unit 112 such that the countershock is discharged as a waveform having a maximum programmable duration of less than 5.99 milliseconds and a tilt of greater than 50%.

MODE OF OPERATION

The implantable defibrillator and the ICD of the present invention are designed to deliver the less-duration pulse (6 milliseconds or less) that the analysis of this invention shows to be more favorable for defibrillation. The analysis draws upon the sources of information in the literature going back a century, and employs mathematical optimization methods to establish the recommended waveforms. In addition to improving defibrillation effectiveness, the pulses of the present invention are more economical with respect both to energy requirements and space requirements. The former permits designing systems for longer life, and the latter permits more flexibility in choosing the implantation site. The lower-energy shocks are also less damaging than those of the prior art.

The maximum energy pulse of the present invention is narrower than prior art maximum energy pulses. The maximum energy pulse for monophasic is about 19–23 joules and for biphasic is about 24–26 joules. The narrow pulse widths are for a typical 50 ohm load. For an extremely high resistance load, such as 100 ohms, the pulse widths will be slightly larger. The internal maximum voltage is in a range of 700–1,000 volts, while 750 volts is one preferred voltage. The lower pulse widths are for the first phase if the biphasic pulse is utilized.

Various modifications can be made to the present invention without departing from the apparent scope hereof.

We claim:

1. An improved process for operating an implantable defibrillator system to produce a monophasic truncated capacitive-discharge defibrillation countershock, the implantable defibrillator system being a self-contained human implantable device including a pulse-generating capacitor means for storing an electrical charge, means for internally charging the pulse-generating capacitor means, and means for selectively discharging the electrical charge in the pulse-generating capacitor for a specified pulse duration as a countershock to be delivered through electrodes implanted in a human patient in response to a sensing of a myocardial arrhythmia in the human patient, the improvement comprising the steps of:

selecting a capacitance value and a maximum charging voltage for the pulse-generating capacitor means such that a delivered energy of the countershock is less than 25 joules; and controlling the means for selectively discharging the electrical charge so as to only deliver the countershock as a waveform having a maximum duration of less than 5.99 milliseconds and a tilt of greater than 50%.

2. The process of claim 1 wherein the duration is between 2 and 5 milliseconds.

3. The process of claim 1 wherein the delivered energy of the countershock is less than 18 joules.

4. The process of claim 1 wherein the maximum charging voltage is in a range of 700–1,000 volts.

5. An improved process for operating an implantable defibrillator system to produce a multiphasic truncated capacitive-discharge defibrillation countershock, the implantable defibrillator system being a self-contained human implantable device including a pulse-generating capacitor means for storing an electrical charge, means for internally charging the pulse-generating capacitor means, and means for selectively discharging the electrical charge in the pulse-generating capacitor for a specified pulse duration as a countershock to be delivered through electrodes implanted in a human patient in response to a sensing of a myocardial arrhythmia in the human patient, the improvement comprising the steps of:

selecting a capacitance value and a maximum charging voltage for the pulse-generating capacitor means such that a delivered energy of the countershock is less than 25 joules; and controlling the means for selectively discharging the electrical charge so as to always deliver the countershock as a waveform having a maximum duration of a first phase that is less than 5.99 milliseconds and a tilt greater than 50%.

6. The process of claim 5 wherein the duration is between 2 and 5 milliseconds.

7. The process of claim 5 wherein the delivered energy of the countershock is less than 18 joules.

8. The process of claim 5 wherein the maximum charging voltage is in a range of 700–1,000 volts.

9. An improved implantable defibrillator system for producing a truncated capacitive-discharge countershock, the implantable defibrillator system being a self-contained human implantable device including a pulse-generating capacitor means for storing an electrical charge, means for internally charging the pulse-generating capacitor means, and means for selectively discharging the electrical charge in the pulse-generating capacitor for a specified pulse duration as a countershock to be delivered through electrodes implanted in a human patient in response to a sensing of a myocardial arrhythmia in the human patient, the improvement comprising:

the means for selectively discharging the electrical charge including means for delivering the countershock as a waveform having a maximum programmable duration of less than 5.99 milliseconds and a tilt of greater than 50%;

the pulse-generating capacitor means having an effective capacitance value and a maximum charging value such that the countershock has a delivered energy of less than 25 joules.

10. The system of claim 9 wherein the duration is between 2 and 5 milliseconds.

11. The system of claim 9 wherein the delivered energy of the countershock is less than 18 joules.

12. The system of claim 9 wherein the waveform is a biphasic pulse and the duration is for a first phase of the biphasic pulse.

13. The system of claim 9 where the duration of the waveform is greater than 1 millisecond.

14. The system of claim 9 wherein the maximum charging voltage is in a range of 700–1,000 volts.

* * * * *